United States Patent [19]

Gieskieng

[11] Patent Number: 4,459,103

[45] Date of Patent: Jul. 10, 1984

[54] AUTOMATIC VOLATILE MATTER CONTENT ANALYZER

[75] Inventor: David H. Gieskieng, Arvada, Colo.

[73] Assignee: Hazen Research, Inc., Golden, Colo.

[21] Appl. No.: 356,858

[22] Filed: Mar. 10, 1982

[51] Int. Cl.³ .................. C21D 11/00; F27B 9/40
[52] U.S. Cl. .......................... 432/43; 266/87; 373/136; 374/180; 432/45
[58] Field of Search ............. 374/157, 139, 180, 26; 136/229, 234, 232, 230; 164/154, 449; 266/87; 432/43, 45

[56] References Cited

U.S. PATENT DOCUMENTS

| | | | |
|---|---|---|---|
| 2,864,878 | 12/1958 | Dalglish | 136/229 |
| 3,444,740 | 5/1969 | Davis | 136/230 X |
| 3,463,005 | 8/1969 | Hance | 374/157 X |
| 3,598,386 | 8/1971 | Murphy | 266/87 X |
| 3,653,262 | 4/1972 | Ehrenfried et al. | 374/142 |
| 4,223,549 | 9/1980 | Kitzinger | 374/142 X |
| 4,330,808 | 5/1982 | Sawada et al. | 73/28 |
| 4,358,948 | 11/1982 | Plessers | 374/26 |

Primary Examiner—Daniel M. Yasich

[57] ABSTRACT

An analyzer is provided for use in determining the volatile matter content of coal and coke. The analyzer automatically adjusts a position of a crucible containing a coal or coke sample relative to a furnace depending upon the temperature of the crucible. The crucible is supported and the temperature of the crucible and sample is sensed by means of a thermocouple arranged as a sling for contacting the crucible. The sensed temperature is compared with a predetermined and desired temperature. A comparison difference triggers a vertical movement of the crucible and sample, within the temperature profile of the furnace, using a servomotor until the crucible is positioned such that the sensed temperature and desired temperature correspond.

16 Claims, 4 Drawing Figures

AUTOMATIC VOLATILE MATTER CONTENT ANALYZER

FIELD OF THE INVENTION

The present invention relates to an apparatus for use in determining the volatile matter content of coal and coke and, in particular, is directed to a temperature sensing and controlling arrangement, which also functions to support a crucible in which the coal or coke is placed for analysis.

BACKGROUND ART

An empirical distillation method analysis of the volatile matter content of coal and coke samples is intended to provide a measure of the volume of gaseous product, exclusive of the free moisture content, which is produced from such samples under a set of standard heating conditions. The volatile matter content is a parameter used in classifying coals and is significant in determining and designing compatible combustion hardware for use in the coal combustion process.

In the ASTM Standard Test Method for "Volatile Matter In The Analysis Sample of Coal and Coke", D 3175-73 (1973), a method is disclosed for determining the volatile matter content of coal or coke. The method involves weighing the coal sample, heating the coal sample to determine the weight loss after the heating, determining the moisture content of the coal sample using the standard found in ASTM D 3173, and then subtracting the moisture content from the weight loss. For the heating step, an operator determines, beforehand, the approximate desired position of the coal sample in a vertical tubular furnace by using a portable thermocouple. The thermocouple is not connected to the crucible but is, typically, a separate device inserted by the operator into the furnace for use in determining the temperature profile therein. In another known embodiment, a thermocouple device is connected to the furnace itself for providing an indication of the temperature thereof at that specific point in the furnace, usually the bottom, so that this may be used to adjust approximately the temperature of at least the hottest point of the temperature profile.

An automatic volatile analyzer of coke and coal is described in the EDP catalog with respect to the Preiser/Mineco volatile programmer. The analyzer described includes holding timers for use in determining when to move a crucible containing a coal sample to different positions in a furnace. Different descent rates of the crucible into the furnace area are also provided in this automatic analyzer. This analyzer moves the crucible as a function of time to preselected positions in the furnace. Although these preselected positions in the furnace are expected to be at desired temperatures, this is often not the case.

DISCLOSURE OF THE INVENTION

In accordance with the present invention, an apparatus is provided for use in analyzing the volatile matter content of coal and coke. The apparatus includes a loosely covered crucible for holding a small sample of coal or coke. A thermocouple-sling combination is releasably joined to the crucible for supporting the crucible. The thermocouple sling is fastened to a motorized suspension and wired to a recorder device. The crucible is vertically movable within a tubular furnace by using the servomotor. The thermocouple sling combination provides a sensed temperature signal of itself and consequently is indicative of the temperature of the crucible it contacts and the sample contained therein. The movement of the crucible in the vertical direction can be made to be a function of the temperature sensed by the thermocouple sling. The servomotor is controlled by a controlling/timing circuit using the temperature signal.

More particularly, the thermocouple sling of the present invention includes two dissimilar metals, in this case Chromel and Alumel, to generate a sensed temperature millivoltage signal relating to the temperature of the thermocouple sling, crucible, and the sample. The sensed temperature signal is inputted to the recorder device which in addition to recording, outputs a voltage somewhat proportional to the sensed temperature. The temperature-related voltage provided by a recorder retransmitting slidewire is compared with one or more predetermined adjustable voltages chosen to correspond to desired temperature levels or set-points. Any difference between the sensed temperature and the target temperatures is translated into movement of the crucible to a different height within the furnace. Specifically, if the thermocouple sling sensed temperature is less than the target or set-point temperature, the servomotor is activated to lower the crucible relative to the furnace to expose it to higher heat. Conversely, if the sensed temperature is greater than the predetermined desired temperature, the servomotor is activated to raise the crucible relative to the furnace. In such a manner, the temperature to which the coal sample is subjected can be controlled at one or more temperature set-points for predetermined time periods to assure a proper determination of volatile matter content.

In view of the foregoing, it is readily seen that a number of advantages of the present invention are achieved. An apparatus is provided for automatically sensing and controlling the temperature of a coal sample to determine its volatile matter content. More significant, a thermocouple sling provides two important functions. The thermocouple sling not only senses the temperature to which the coal sample is being subjected but also acts to support the crucible and coal sample held by the crucible, providing a contact measurement of the crucible temperature and hence the temperature of the contained sample. In addition, this analyzer automatically moves the vertical position of the crucible and coal sample as a function of temperature, unlike previous devices which rely solely on predetermined positions in a furnace. Use of the present invention permits rapid and accurate testing of volatile matter content of a coal sample, since the reproducibility of test results is maximized because of the increased precision in temperature control and heating rates.

Additional advantages of the present invention will become readily apparent from the following discussion when taken in conjunction with the accompanying drawings.

DESCRIPTION OF THE PREFERRED EMBODIMENTS

Figure 1:
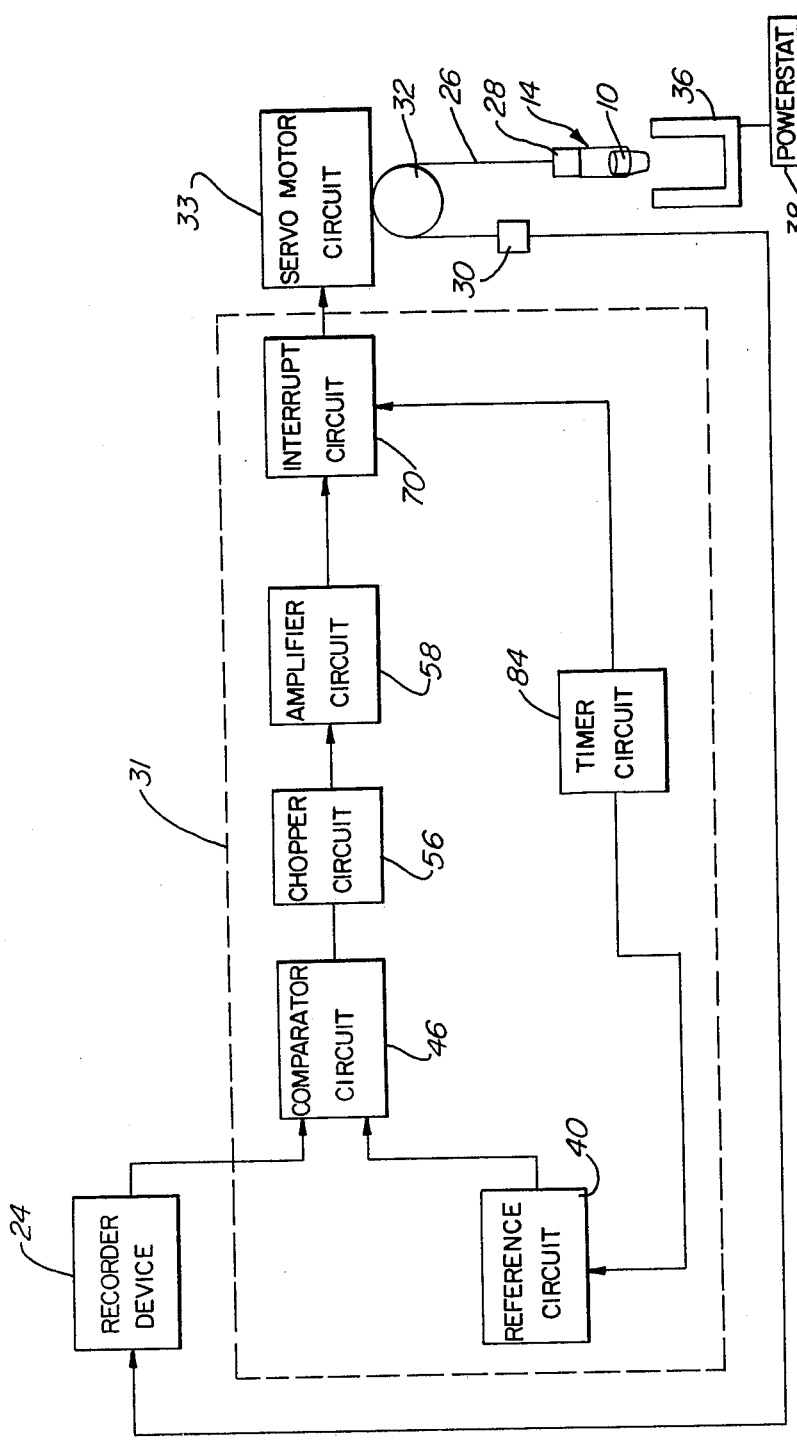
FIG. 1 is a block diagram of the present invention.
Figure 2:
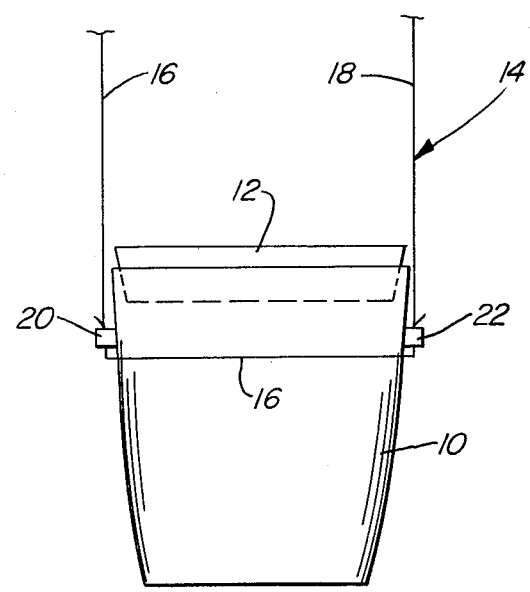
FIG. 2 is an enlarged, fragmentary, side elevational view of the thermocouple sling supporting a crucible.
Figure 3:
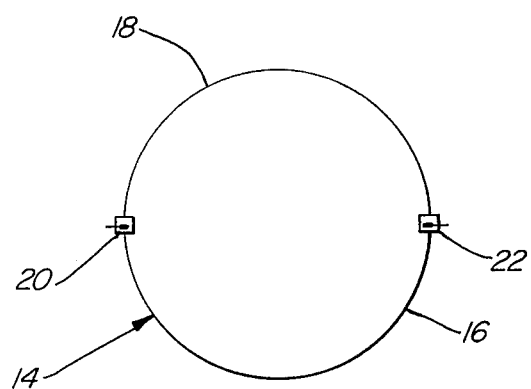
FIG. 3 is a bottom plan view of the thermocouple sling without the crucible.

In accordance with the present invention, an apparatus for use in empirically detemining the volatile matter content of a coal or coke sample is provided. With reference to FIGS. 1, 2, and 3, the apparatus includes a crucible 10 having a slightly loose cover 12 for holding or containing the sample of coal or coke. The crucible 10 is releasably supported by a thermocouple mechanism in the form of a thermocouple sling 14. The thermocouple sling 14 includes two dissimilar metal elements 16, 18. In the preferred embodiment, the two metal elements are Alumel and Chromel. As can best be seen in FIGS. 2 and 3, the two elements 16, 18 are joined together to form thermocouple junctions 20, 22 using "Quiktip" connectors. The two thermocouple junctions 20, 22 contact or touch the crucible 10 and are used to sense the temperature of the crucible 10. It is also appreciated that since the thermocouple junctions 20, 22 contact the crucible 10 containing the sample, the thermocouple junctions 20, 22 also provide an indication of the temperature of the sample. The sensed temperature signals from the two thermocouple junctions 20, 22 are averaged to provide a single sensed temperature signal. Portions of the two elements 16, 18 are formed in the shape of a semi-circle and connected together at the thermocouple junctions 20, 22 to provide an opening for receiving the crucible 10. The elements 16, 18 then extend upwardly to be electrically connected to a recorder device 24 through a flexible electrically insulated conductor 26 weighted on each end by the masses of weights 28, 30. The recorder device 24 provides a visual indication of the temperature sensed by the thermocouple sling 14 as well as making a pen recording on a strip chart.

From the recorder device 24, an electrical representation of the sensed temperature signal is obtained from its retransmitting slide wire and is applied to a controlling/timing circuit 31 of FIG. 1. The controlling/timing circuit 31 controls the energization or activation of a servomotor circuit 33 according to preplanned setpoints and periods of time. The servomotor circuit 33 is operatively connected to a pulley 32 about which the insulated conductor 26 is wrap hung. The insulated flexible conductor 26 carries the sensed temperature millivoltage signal to the recorder device 24. The servomotor circuit 33 is used to turn or rotate the pulley 32 clockwise or counterclockwise for raising or lowering thermocouple sling 14, crucible 10 and the sample contained therein in a substantially vertical direction with respect to a tubular furnace 36. The temperature of the tubular furnace is initially regulated by a powerstat 38 and left set.

The furnace 36 has a temperature profile with the hottest part located at he bottom thereof. Preferably, one portion or level of the furnace 36 has a temperature of 600° C. and another lower level or portion of the furnace 36 has a temperature of 950° C. It has been found that an accurate determination of volatile matter content of coal and coke can be made when a sample thereof is subjected to heat at these two different temperatures for preselected time periods.

Figure 4:
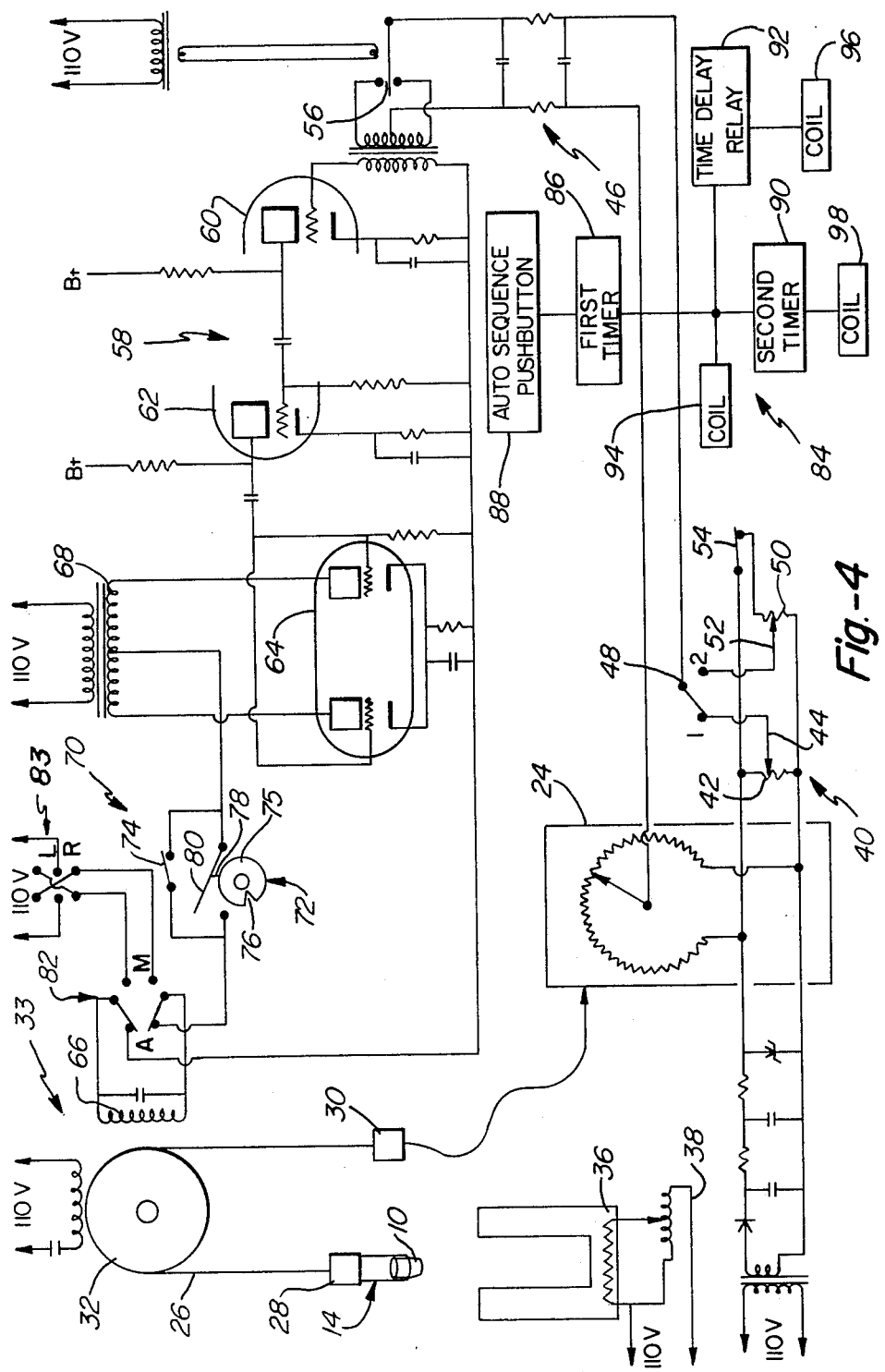
FIG. 4 is a detailed schematic of the controlling/timing circuit of the present invention.

Referring now also to FIG. 4, as well as FIG. 1, a more detailed representation of an embodiment of the present invention is shown. The controlling/timing circuit 31 of FIG. 1 includes reference circuit 40. The reference circuit 40 includes a first variable resistor 42 which includes a sliding contactor 44 positioned at a predetermined position along the resistor 42 so that a first reference temperature signal voltage corresponding to a first predetermined and desired temperature is picked off and applied to a comparator circuit 46. The reference circuit 40 also includes a relay 48 for switching between the first reference temperature signal and a second predetermined reference signal, which is provided by means of a second variable resistor 50 having a sliding contactor 52. The reference circuit also includes a relay 54 for removing the excitation of variable resistor 50 at a later preselected time. In the preferred embodiment, the first reference temperature signal corresponds to a temperature of 600° C. and the second reference temperature signal corresponds to a temperature of 950° C.

The comparator circuit 46 also receives a retransmitted temperature related signal from the recorder device 24, which is basically responsive to the temperature detected by the thermocouple sling 14. The comparator circuit 46 outputs a temperature difference signal primarily representing the polarity of the difference between the retransmitted temperature related signal and the selected one of the two reference signals. This temperature difference signal is modified by a chopper circuit 56. The chopper circuit 56 is a vibrating switch energized at the line frequency. The switch chopped pulses of the temperature difference signals are thereby synchronized with the sinusoidal variation of the line power. The phase relationship of these pulses to the line power then depends upon the positive or negative difference between the sensed temperature signal and the reference signal.

The pulsed output from the chopper circuit 56 is applied to an amplifier circuit 58 including voltage amplifiers 60, 62 for the necessary voltage amplification of the pulsed output. A power amplifier 64 of the amplifier circuit 58 is for generating sufficient power to drive servomotor winding 66 with pulses corresponding to the positive or negative portion of the sinusoidal voltage provided by transformer 68. However, the power amplified pulses are transmitted through an interrupt circuit 70. The interrupt circuit 70 includes a motor driven cam switch 72, and a shorting relay 74, the contacts of which are connected across the contacts of the motor cam switch 72 to stop the interruptor action of the interrupt circuit 70 when required. Whenever a cam 75 of cam switch 72 has rotated such that a notch 76 formed in the cam 74 receives a finger 78, a contact 80 provides an electrical connection between the transformer 68 and a selector switch 82 to provide power to the power amplifier 64 and servomotor circuit 33, when the selector switch 82 is in an "auto" position. The "auto" position provides an automatic mode of moving the crucible 10, the movement depending upon the temperature of the crucible 10 and the magnitudes of the reference signals as well as the controlling/timing circuit 28. The interrupt circuit 70 provides short, infrequent pulse driving of the servomotor of the servomotor circuit 30 so that the temperature of the crucible 10 and thermocouple sling 14 has sufficient time to equilibrate or settle prior to the next pulsed movement, so that the next movement, if required, will be in the proper direction.

The direction of movement of the pulley 32, referencing FIG. 4, hence the direction of vertical movement of the crucible 10 and thermocouple sling 14 depends upon the polarity of the pulses outputted by the chopper circuit 56, which determines the phase relationship of the amplified pulses reaching the windings 66 of the servomotor. When the pulses have a negative polarity indicating that the reference signal is greater in magnitude than the magnitude of the sensed temperature signal, the phase of the voltage across the windings 66 is such that the pulley 32 is driven in a counterclockwise direction by the servomotor, lowering the crucible 10 and thermocouple sling 14 into hotter areas of the furnace. Conversely, when the pulses have a positive sense indicating that the reference signal is less in magnitude than the magnitude of the sensed temperature signal, the phase of the voltage applied across the windings 66 is such that the pulley 32 is driven in a clockwise sense by the servomotor, raising the crucible 10 and thermocouple sling 14 into cooler areas of the furnace, or at the end out of the furnace.

As illustrated in FIG. 4, the energization of the coils associated with the relays 48 and 74 is controlled by the timer circuit 84, assuming the selector switch 82 is in the "auto" mode. The timer circuit 84 includes a first timer 86 which is enabled by pushbutton 88, and begins to count down from a predetermined stored count with relay 48 connected to the first set-point reference of sliding contactor 44 and the interruptor bypass relay 74 in its open position. The first timer 86 is coupled to a second timer 90, a time delay relay 92 and a coil 94. When the predetermined time set in the first timer 86 is completed, the output from the first timer energizes the coil 94. The energization of this coil 94 changes the state of the relay 48 so that the first reference is disconnected and the second reference signal is applied to the comparator circuit 46. Further, when the first timer 86 times out, the second timer 90 is enabled to count down for its predetermined time interval. At the beginning of the second timer 90 predetermined time interval, time delay relay 92 energizes relay coil 96 for six (6) seconds. While the coil 96 is energized, the relay 74 is closed and the interrupting action of the cam switch 72 is bypassed, so that the servomotor drives continuously as there is a difference signal from the comparator circuit 46, caused by relay 48 shifting to the set-point of sliding contactor 52, which is higher than the previous set-point of sliding contactor 44. This permits the servomotor to quickly drive the crucible 10 to the temperature area corresponding to the second set-point, which requires about 6 seconds, after which time delay relay 92 times out, opening relay 74, thereby re-enabling cam switch 72. The second timer 90 continues to operate through the remainder of the desired high temperature period and when it times out coil 98 is energized. The energization of coil 98 switches open the state of relay 54 so that a zero reference signal is applied to the comparator circuit 46. In this state of the relay 54, as well as relay 48, and the contact interruptor 80 bypassed, the crucible 10 and sample are quickly moved in a vertically upward direction out of the furnace to where the servomotor runs into a mechanical stop.

To further understand the present inventions, a typical test process is now described. Initially, power is applied to the furnace 36, the selector switch 82 is placed in "manual" mode, and the thermocouple sling 14 is moved using the selector switch 82 and switch 83 to the bottom of the furnace 36, without the crucible 10 held thereby, where the furnace 36 is the hottest. When the thermocouple sling 14 detects a temperature of about 15° C. above the second predetermined reference temperature (950°+15° C.), the thermocouple sling 14 is then moved upwardly while still under manual control. The movement of the thermocouple sling 14 is halted when it is approximately 1.5 inches above the furnace 36. Next, the thermocouple sling 14 receives the crucible 10 containing a weighted sample of coal or coke. The selector switch 82 is then set to its "automatic" mode with the switch contacts positioned as illustrated in FIG. 4. At this time, the comparator circuit 46 compares the sensed temperature signal indicative of a temperature of approximately 100° C., from the recorder device 24, with the first reference signal corresponding to 600° C. The first timer 86 is then enabled with pushbutton 88 and begins to count down from its preset time period. In the preferred embodiment, the first timer 86 is set for about six (6) minutes.

Initially during this six minute time period, since the thermocouple sling 14 and crucible 10 are above the furnace 36 and now at a temperature of about 100° C., the first reference signal is greater in magnitude than the sensed temperature signal. As a result, downward motion phased pulses are generated by the chopper circuit 56 and amplified for driving the servomotor through the cam switch 72, and the servomotor of the servomotor circuit 30 is driven in a downward direction for a 1/10 second interval during each revolution of the cam 75. In a preferred embodiment, the cam 75 rotates one complete revolution each twelve (12) seconds. The interruptor contact 80 provides a relatively slow descent of the crucible 10 into the furnace 36 because of the intermittent energization of the servomotor. This permits orderly venting of evaporating moisture and other low boiling fractions. If these were allowed to erupt by a faster temperature rise, some sample material would be blown out of the crucible 10 thereby destroying the test.

The sensed temperature of the thermocouple sling 14 corresponds to the first reference temperature of 600° C. after about five minutes of intermittent descent into the furnace 36, because at this time thermocouple junctions 20, 22 are positioned in the furnace 36 at its 600° C. level. This temperature is maintained for the remaining one minute of the six minute time period. This temperature is maintained by comparing the sensed temperature signal with the first reference signal. Any difference in magnitude between the sensed temperature signal and the first reference signal is used to vertically adjust the position of the crucible 10. The direction of vertical movement of the crucible 10 and thermocouple sling 14 depends upon the polarity of the pulses outputted from the chopper circuit 56.

At the completion of this first six minute time period, the second timer 90 and time delay relay 92 are enabled. The second timer 90 has a time period of about six minutes associated therewith. With the activation of the second timer 90, the coil 96 is also energized which closes relay 74 for the six second duration of the time delay relay 92. In addition, coil 94 is energized so that relay 48 changes state and the first reference signal is removed and the second reference signal, corresponding to 950° C., is applied to the circuit 46. With the closure of relay 74 and the changing to the second reference signal, downward motion phased chopper pulses are continuously applied to the servomotor windings 66 so that the crucible 10 and sample are relatively quickly moved downwardly into the furnace 36. This rapid movement positions the crucible 10 very quickly in that portion of the furnace 36 which is at a temperature of about 950°. Upon completion of this six second time period, the coil 96 is deenergized and the relay 74 opens. Any further vertical adjustment of the crucible 10 is then once again moderated by the cam switch 72 as well as controlled by any pulses outputted by the chopper circuit 56.

The second timer 90 like the first timer 86, also normally has a six (6) minute time period associated therewith. During this period, which begins immediately after the completion of the time period associated with the first timer 86, any necessary vertical adjustment of the crucible 10 is automatically made to maintain the crucible 10 at a temperature of 950° C., the initial adjustment hastened by bypassing for six seconds the cam switch 72 using time delay relay 92. At the completion of this six minute period, the relay 54 opens and the relay 74 is once again closed. When relay 54 is open, the reference temperature signal to the comparator circuit 46 corresponds to a very low temperature and the sensed temperature is much greater than that, causing upward motion chopper pulses. Also, since relay 74 is once again closed, upward phased power pulses are continuously applied to the servomotor circuit 30 through the relay 74 while bypassing the cam switch 72 in order that the crucible 10 may be quickly raised from the furnace 36. The crucible 10 can then be removed from the thermocouple sling 14 for further cooling and subsequent weighing in order to determine the volatile matter content of the sample contained in the crucible 10. The predetermined time periods set in the first and second timers and noted in the foregoing discussion have been empirically determined and the use thereof is intended to maximize the accuracy of the volatile matter content analysis.

In another preferred arrangement, the recorder device 24, the reference circuit 40, the comparator circuit 46, the chopper circuit 56, and the amplifier circuit 58 are time shared with at least two furnaces, servomotor circuits, thermocouple slings, and crucibles. In such an embodiment the interrupt circuit 70 is modified to include a cam switch having two notches, wherein the notches are separated by 180° to provide a pulse every six (6) seconds. Another cam with a 50% down profile and switch are added to effect the transfer of the foregoing control equipment from one furnace to another in a synchronized manner. Consequently, during ½ revolution of the cam switch or every six seconds, vertical adjustment of one of the two crucibles is controlled, while during the second half of the cam revolution the other of the two crucibles can be controlled using the 1/10 second pulses which occur once during each six second period. This arrangement results in the chart of the recorder device 24 being a sequential composite of the two crucible temperatures while doubling the analytical capacity of the apparatus.

Although the embodiments discussed herein have been described or illustrated with reference to particular hardware, such as relays, vacuum tubes and transformers, it is readily appreciated that other appropriate electrical hardware can be utilized. With respect to the recorder device 24, such a device is commercially available from Leeds and Northrup under the name "SPEED-O-MAX H".

Based on the above disclosure, it is readily discerned that a number of worthwhile benefits are achieved in the present invention. A volatile matter content analyzer is provided for automatically adjusting the position of a crucible and a sample relative to a furnace by continually using the temperature sensed by a thermocouple sling. In this regard, the thermocouple sling not only provides a signal relating to the temperature of the crucible and the sample contained therein but also supports the crucible for vertical movement with respect to a furnace. In addition, the control circuitry of the analyzer permits a proper determination of the volatile matter content to be made by regulating the rate of temperature changes and the amount of time that the sample is subjected to predetermined temperatures. Consequently, accuracy of the volatile matter content determination is maximized and reproducibility of results is enhanced. Furthermore, multiple samples can be analyzed simultaneously to increase the analytical capacity and also minimize the amount of hardware needed.

Although the present invention has been described with reference to a plurality of embodiments, it is readily appreciated that variations and modifications can be effected within the spirit and scope of this invention.

What is claimed is:

1. An apparatus for use in analyzing the volatile content of a sample comprising:
   a furnace;
   first means for holding the sample;
   thermocouple means contacting said first means for suspendedly supporting said first means and also providing a temperature signal relating to the temperature of said first means; and
   second means responsive to said temperature signal for adjusting the position of said first means with respect to the furnace.

2. An apparatus for use in analyzing the volatile content of a sample comprising:
   first means for holding the sample relative to a heated container;
   thermocouple means for suspendedly supporting said first means moving therewith and providing a temperature signal relating to the temperature of said thermocouple means; and
   second means in operative association with said thermocouple means for moving said thermocouple means and said first means, the movement of said first means and said thermocouple means depending upon the temperature of said thermocouple means.

3. An apparatus, as claimed in claims 1 or 2, wherein:
   said second means includes means for generating a first reference signal corresponding to a first temperature.

4. An apparatus, as claimed in claims 1 or 2, wherein:
   said thermocouple means includes two dissimilar metal elements joined together at least at one junction.

5. An apparatus, as claimed in claims 1 or 2, wherein said second means includes:
   means for generating a first reference signal corresponding to a first temperature; and
   means responsive to said generating means for comparing the first reference signal with the temperature signal provided by said thermocouple means.

6. An apparatus, as claimed in claims 1 or 2, wherein:
   said second means includes interrupt means for use in intermittently moving said first means.

7. An apparatus for use in both supporting a container and the material contained therein relative to a heating means and providing an indication of the temperature of said container and the material contained therein comprising:

a thermocouple sling in releasable contacting association with the container having material contained therein, said thermocouple sling suspendedly supporting said container and the material contained therein relative to a surface but spaced therefrom, and said thermocouple sling generating a temperature signal relating to the temperature of said container and the material contained therein, whereby means responsive to said temperature signal adjusts the thermocouple sling relative to the container.

8. An apparatus, as claimed in claim 7, wherein:
said thermocouple sling includes at least one thermocouple junction where two dissimilar metals are joined together, said thermocouple junction adapted to contact said container.

9. An apparatus, as claimed in claim 7, wherein:
said thermocouple sling includes first and second metals arranged to form an opening between portions of said metals, said opening adapted to receive said container.

10. In a system for determining the volatile matter content of a coal or coke sample including a furnace, a crucible for holding the sample, and means for use in moving the crucible and sample, a device comprising:
a thermocouple sling in releasable operative association with said crucible for contacting and suspendedly supporting said crucible, said thermocouple sling being movable by said moving means with respect to said furnace together with said crucible and said sample, and said thermocouple sling generating a temperature signal relating to the temperature of said crucible, said sample, and said thermocouple sling for controlling movement of said moving means in response to said temperature signal.

11. A device, as claimed in claim 10, wherein:
said thermocouple sling includes at least one thermocouple junction where two dissimilar metal elements are joined together, said thermocouple junction contacting said crucible.

12. A device, as claimed in claim 10, wherein:
said thermocouple sling includes first and second metal elements arranged to form an opening between portions of said metal elements, said opening adapted to receive said crucible.

13. An apparatus for use in analyzing the volatile content of a sample adapted to be positioned relative to a furnace, comprising:
furnace means supported on a surface;
container means for holding the sample;
a thermocouple sling in contacting association with said container means for use in suspendedly supporting said container means and for providing a temperature signal relating to the temperature of the sample; and
driving means in operative association with said thermocouple sling for moving said container means and said thermocouple sling relative to said furnace means depending upon the temperature signal.

14. An apparatus, as claimed in claim 13, and further comprising:
first means for generating a reference signal;
second means responsive to said first means for comparing the reference signal to the temperature signal and for providing an output signal; and
third means communicating with said second means for intermittently applying the output signal from said second means to said driving means.

15. An apparatus, as claimed in claim 14, wherein:
said thermocouple sling includes at least one thermocouple junction where two dissimilar metal elements are joined together, said thermocouple junction contacting said container means.

16. An apparatus for use in analyzing the volatile content of a sample comprising:
furnace means supported on a surface;
container means for holding the sample;
a thermocouple sling in contacting association with said container means for use in suspendedly supporting said container means, moving therewith and providing a temperature signal relating to the temperature of the sample;
driving means in operative association with said thermocouple sling for moving said container means and said thermocouple sling relative to said furnace means depending upon the temperature signal;
first means for generating a reference signal;
second means responsive to said first means for comparing the reference signal to the temperature signal and for providing an output signal; and
third means communicating with said second means for intermittently applying the output signal from said second means to said driving means to move said container means and said thermocouple sling;
said thermocouple sling includes at least one thermocouple junction where two dissimilar metal elements are joined together, said thermocouple junction adapted to contact said container; and
said thermocouple sling includes first and second metal elements arranged to form an opening between portions of said metal elements, said opening adapted to receive the crucible.

* * * * *